United States Patent
Johansen

(10) Patent No.: US 6,773,685 B2
(45) Date of Patent: Aug. 10, 2004

(54) APPARATUS FOR STERILIZING DENTAL HANDPIECES

(76) Inventor: Peter Johansen, Strandvejen 126, DK-8000 Århus C (DK)

( * ) Notice: Subject to any disclaimer, the term of this patent is extended or adjusted under 35 U.S.C. 154(b) by 0 days.

(21) Appl. No.: 09/727,678

(22) Filed: Dec. 4, 2000

(65) Prior Publication Data

US 2002/0068029 A1 Jun. 6, 2002

(51) Int. Cl.[7] .............................. A61L 2/00; A61L 9/00; B08B 3/00
(52) U.S. Cl. ........................ 422/295; 422/297; 422/298; 422/300; 422/305; 422/307; 134/170; 134/171
(58) Field of Search .............................. 422/26–28, 257, 422/260, 266, 285, 288, 292, 295, 297–301, 305–307; 134/170–171

(56) References Cited

U.S. PATENT DOCUMENTS 5,057,283 A * 10/1991 Guggenheim et al.
5,380,369 A * 1/1995 Steinhauser et al.
5,552,113 A * 9/1996 Jennings

* cited by examiner

Primary Examiner—Robert J. Warden, Sr.
Assistant Examiner—Monzer R. Chorbaji
(74) Attorney, Agent, or Firm—Browdy and Neimark, P.L.L.C.

(57) ABSTRACT

An apparatus for disinfecting and sterilizing dental handpieces includes a treating chamber with an internal holding stub which has through-channels for connecting exterior treatment fluid source elements to internal standard channels in and through the handpieces to through-flush treatment fluid through these channels from a socket end to a tip end of the handpiece. The treating chamber is laid-out as a pressure resistant autoclaving chamber provided with steam generation at elevated temperature and pressure. The through-channels of the holding stub are alternatively connectable through an outlet valve to the exterior atmosphere so as to enable back-flushing of pressurized steam from the treating chamber through the internal channels from the tip end to the socket end.

5 Claims, 4 Drawing Sheets

US 6,773,685 B2

APPARATUS FOR STERILIZING DENTAL HANDPIECES

FIELD OF THE INVENTION

The present invention relates to an apparatus for disinfecting and sterilizing dental handpieces. These instruments are characteristic in having narrow, through-going channels for cooling water and for either a rotary driving shaft for a drilling head or for an air flow for driving a turbine. A need has arisen for effecting a complete disinfection/sterilization of these instruments between uses for successive patients, and different systems for this purpose have already been developed, see for example EP-B-0,300,945 and U.S. Pat. No. 5,552,113.

BACKGROUND OF THE INVENTION

In connection with the invention special attention if paid to the system type, in which the instruments are subjected to autoclaving, preferably after a flush cleaning of the channels. By the autoclaving and the associated generation of steam the exterior surfaces of the instruments will be effectively sterilized, but an effective sterilization of the channels will not be automatically effected thereby.

According to U.S. Pat. No. 5,552,113 it is proposed to feed the steam into the autoclaving chamber by forcing the steam through the said channels from an exterior steam generator, but even though the channels may thereby be effectively sterilized, the general autoclaving of the instruments will be inferior to what is achievable in an ordinary autoclave, where the steam is generated inside the treating chamber, in which the sterilizing effect, widely due to condensation on the instruments, is more pronounced. Such a "primary" autoclaving with internal steam generation is know from WO 96/00534, where the inlets to the channels in relevant instrument holders or adaptors are used for letting in flushing water, whereby this flushing water is collected in the treating chamber and subsequently heating inside that chamber for primary steam generation therein.

SUMMARY OF THE INVENTION

With the present invention is has been recognized that the inlet to the narrow channels, normally comprising a holding stub sealingly communicating with the channels at the handle root end of the instrument and, itself, being connected with relevant supply sources through pipe or hose means, may alternatively be used as an outlet, namely by a forcing out of autoclave steam from the treating chamber through the narrow channels. This may be arranged without any kind of connector means between the treating chamber and the free tips of the instruments since these, as far as the steam is concerned, will be inherently exposed to the steam pressure inside the chamber. Of course, any inlet connection in the holding stub, if also used for outletting purposes, should be connectable to the relevant channels means through a valve system for connecting the channel means selectively to an inlet medium source or to a drain outlet.

Another feature of the present invention is that use is made of an external steam generator, preferably mechanically built directly together with the treating chamber and delivering the steam directly into the treating chamber, thus avoiding special pipe or hose connections between the steam generator and each of the instrument holding stubs.

Additionally, the delivery of the steam from the external steam generator, in which the steam temperature and pressure can be brought up to a relatively very high level, will condition a high degree of temperature control with respect to the temperature of the steam as passing through the said channels, inasfar as any relevant temperature sensor can be placed in the treating chamber itself and not in connection with the channels or associated steam supply pipe means.

BRIEF DESCRIPTION OF THE DRAWINGS

In the following the invention is described in more detail with reference to the drawing, in which.

DETAILED DESCRIPTON OF THE INVENTION

Figure 1:
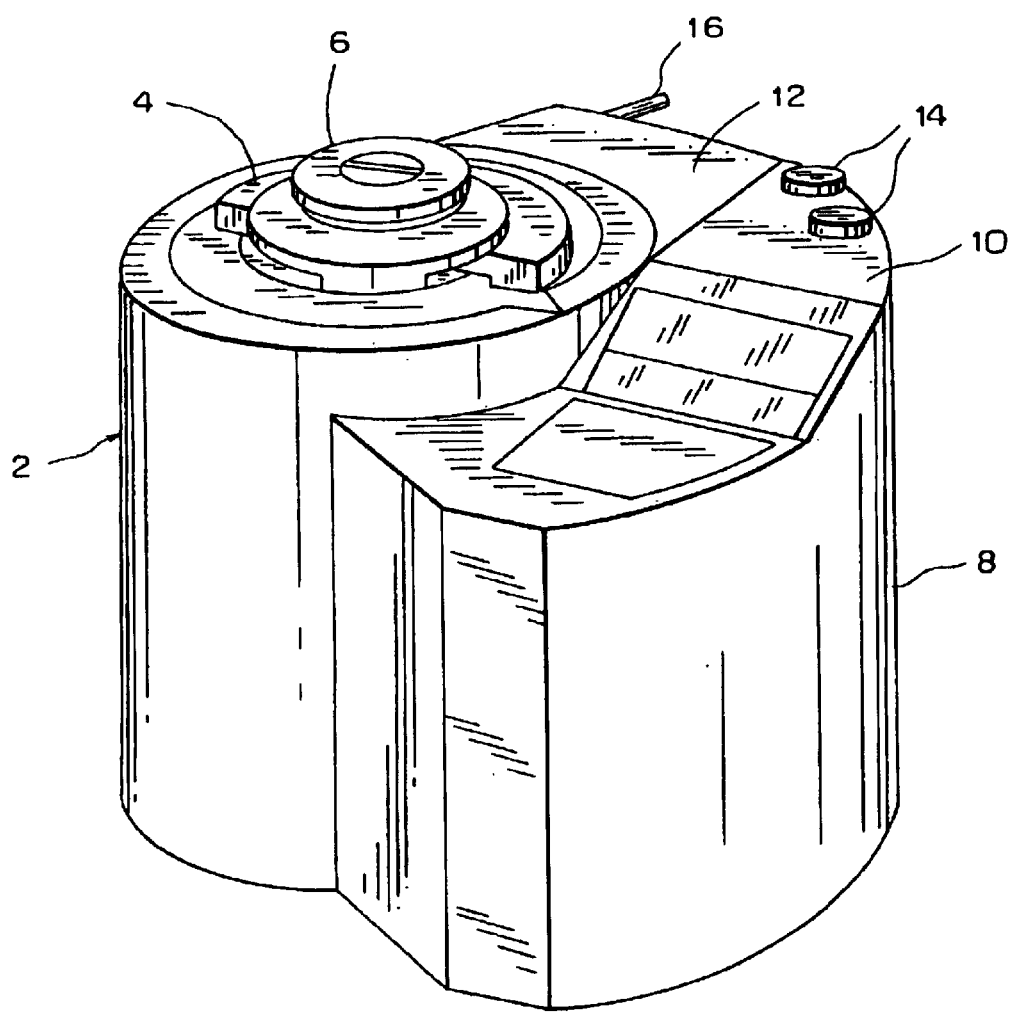
FIG. 1 is a perspective view of an apparatus according to the invention.

The apparatus illustrated comprises a cylindrical treating housing 2 covered by a lid 4 with a handle knob 6 and being integrally connected with a programming housing 8, a tank housing 10 and an operation housing 12 holding the relevant valve and other operational equipment. The tank housing 10 has removable lids 14 for providing access to tank units for water and oil, respectively. The operation housing has a stub 16 for hose connection with an exterior pressurized air system.

Figure 2:
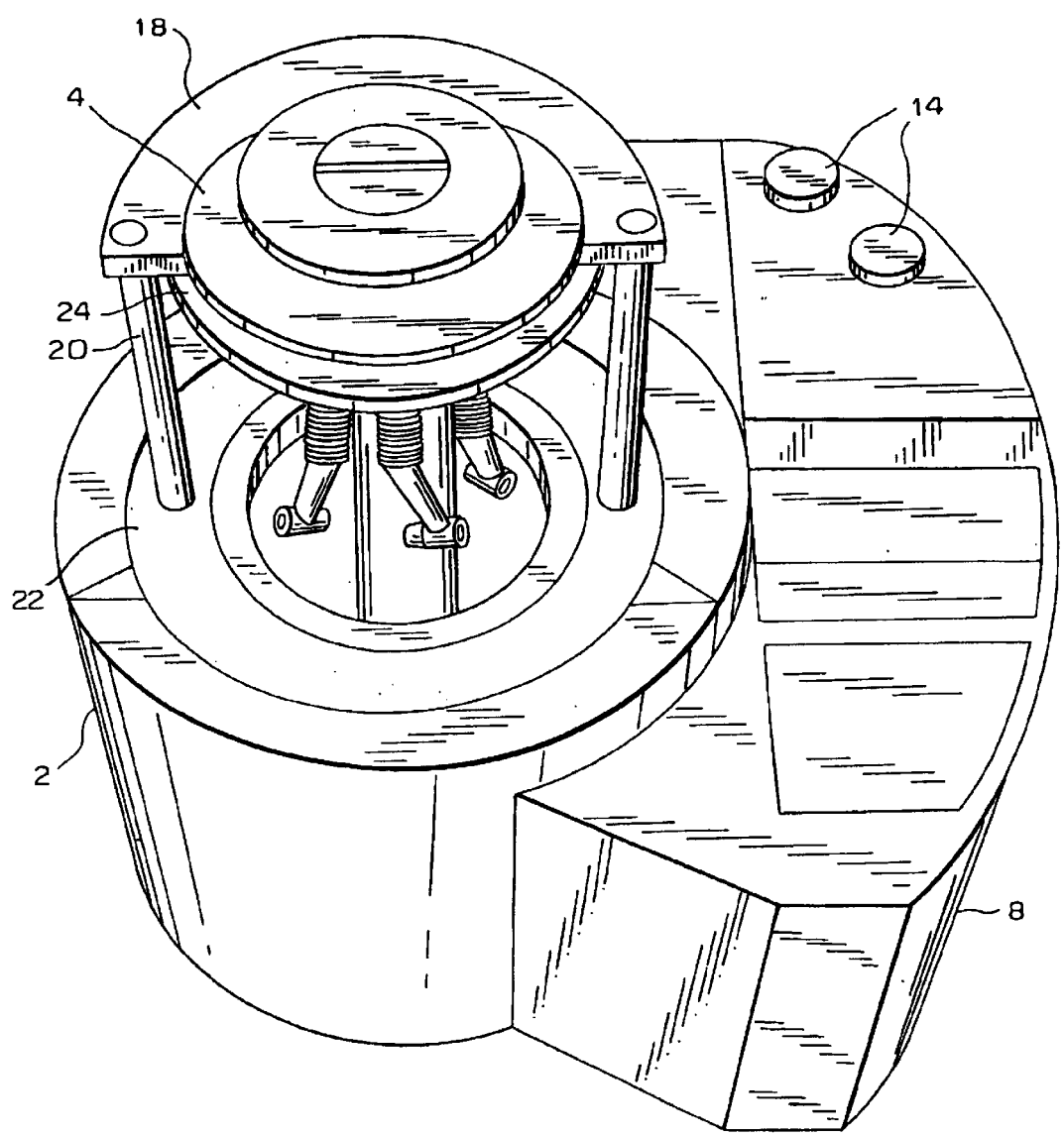
FIG. 2 is a similar view of a treating chamber thereof, shown in partly opened/closed condition.

As indicated in FIG. 2 the lid 4 is mounted in a half-circular holder ring 18, which is connected with the treating housing 2 by means of two opposed carrier rods 20 or three such rods, which can be raised and lowered by non-illustrated actuator means in the treating housing. The latter comprises a central, upwardly open cylinder chamber 22, which is tightly closable by a lower disc member 24 connected with the lid 4. The inner edge of the semi-circular holder ring 18 is received in an annular groove between the overlying lid plate 4 and the underlying disc member 24, such that the lid structure as a whole may be laterally displaced out of and into an operative position centrally engaged with the raisable/lowerable system 18, 20.

Figure 3:
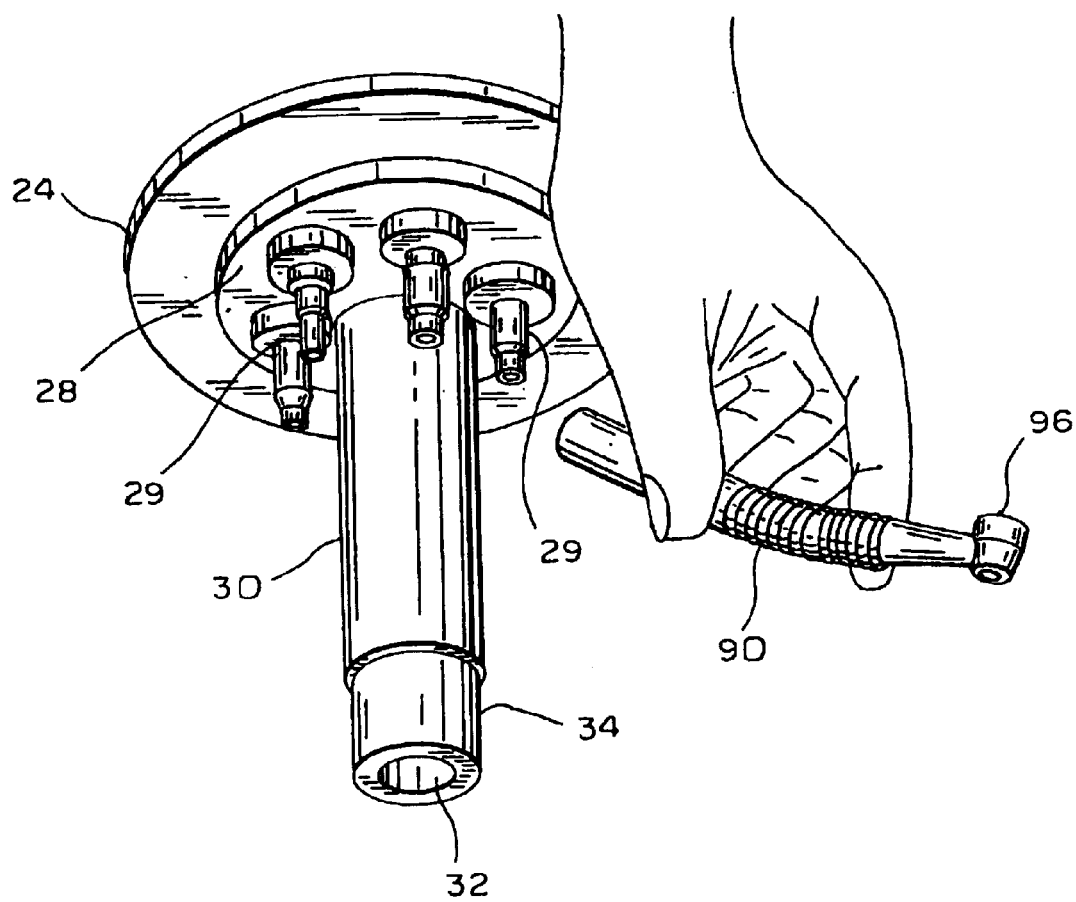
FIG. 3 is a similar view of an instrument holder thereof.

FIG. 3 shows that the lid disc member 24 has an outer sealing ring 26 for sealing against the top of the treating housing and a central block member 28 provided with an annular row of downwardly protruding adaptors 29 for receiving the handle ends of the dental instruments. These adaptor or connector stubs 29 are designed just as the corresponding stubs on their associated handle elements, with sealed ring zones enabling communication between parallel input channels (from above) and more or less parallel, internal channels in the instruments, when socket portions of these are pushed into holding engagement with the stubs, no matter how the instruments are rotationally oriented.

As already disclosed in the relevant prior art, see e.g. U.S. Pat. No. 5,380,369, it is perfectly possible to interconnect a number of such holding stubs by means of a channel system inside a common carrier block 28 in such a manner that the relevant individual channels in the instruments will be connected in parallel, typically a central "driving" channel either for a mechanical driving shaft leading to a drilling head or for guiding a pressure fluid to a driving turbine in a drilling head, and an eccentic "spray" channel for guiding a cooling fluid to the drilling area.

Thus, only two main channels will be sufficient to communicate with all of the holding stubs, and in the assembly shown in FIG. 3 the block member 28 is provided with a downwardly projecting central rod 30, in which these channels are provided, ending inside a bottom socket opening 32.

Figure 4:
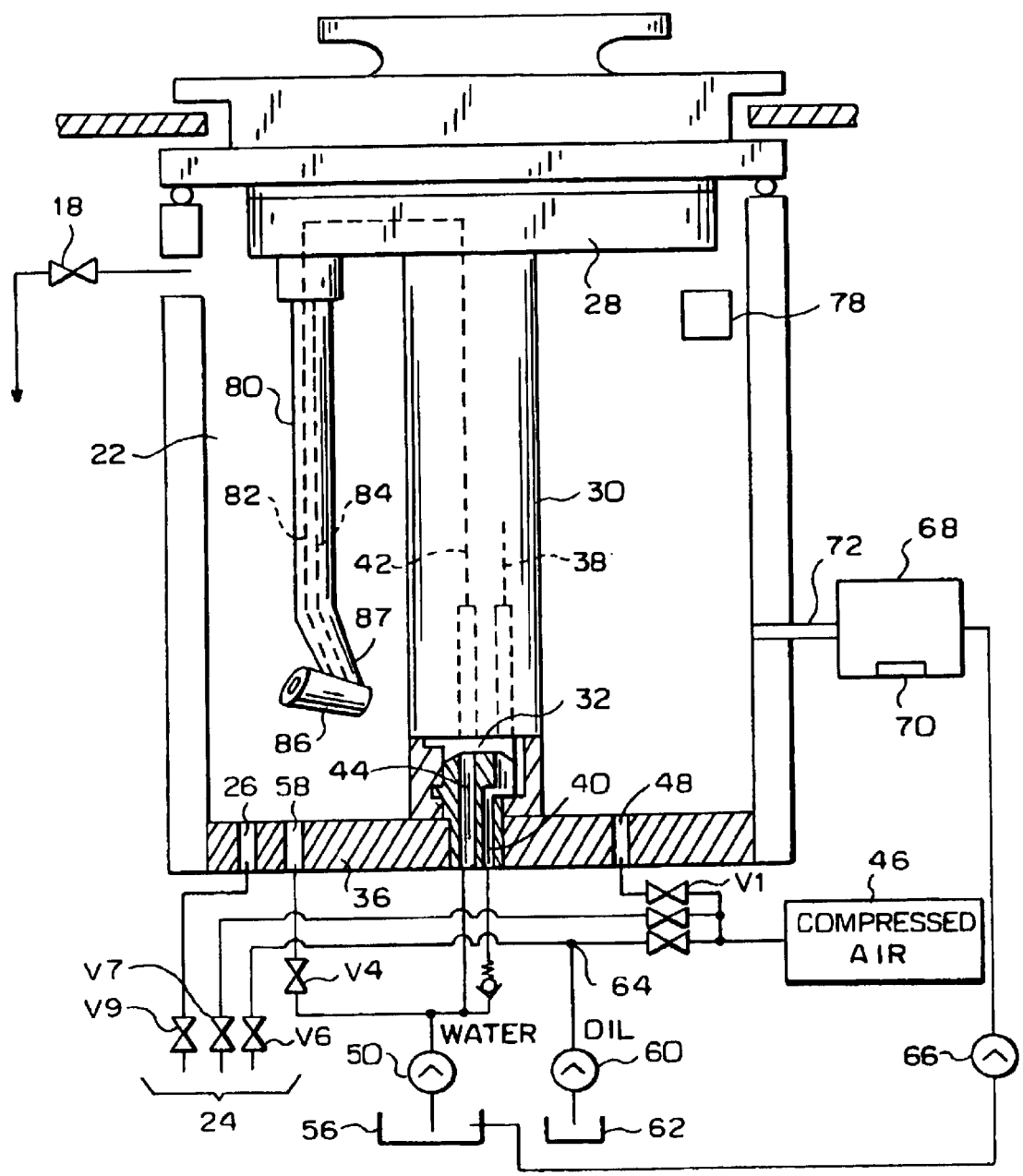
FIG. 4 is a diagrammatic view of the apparatus.

As shown in FIG. 4, when the central rod 30 is lowered in connection with the lowering of the lid structure, the lower socket opening 32 of the central rod 30 will be received over a connector stub 34 projecting from a fixed bottom plate 36 of the chamber 22. Through this stub 34 a drive channel 38 in the rod 30 is connected to a throughbore 40 of the stub, while a flush channel 42 is connected to a throughbore 44. The bores 40 and 44 are connected to respective stop valves V2 and V3 which are in turn connected to a source 46 of compressed air. This source 46 is also, via a valve V1, connectable to a channel 48 through the bottom plate 36.

The bore 44 is connected to a water pump 50 through a channel 52, and also the bore 40 is connected to this pump, only through a check valve 54. The pump 50, pumping from a water tank 56, is additionally, through a valve V4, connected to a channel 58 through the bottom plate 36.

An oil pump 60 pumping from an oil tank 62 is at point 64 connected to the channel system at the left hand end of the valve V2.

A second water pump 66, also pumping from the water tank 56, is arranged for pumping water to a steam generator 68, which is provided with a heating element 70 and is connected 30 to the treating chamber 22 through a conduit 72. At its top end the chamber 22 is connected with a venting valve V8.

The two connector bores 40 and 44 are connected directly, through respective valves V6 an V7, to a drain outlet 74, to which also a drain channel 76 through the chamber bottom 36 is connected via a valve V9.

The treating chamber 22 is provided with pressure and/or temperator sensing means 78.

In FIG. 4 it is shown that a relevant dental instrument 80 is mounted on a selected holder and connector stub 29 (FIG. 3), this instrument having interior channels 82 and 84 for driving air to a turbine in a drilling head 86 and cooling water to a spray orifice 87, respectively. Through the upper block member 28 and the channel 42 in the rod 30 the cooling channel 84 will be connectable with the connector bore 44, while the drive channel 82 is correspondingly connectable, through the rod channel 38, to the connector bore 40.

In operation, the following steps are to be effected:

1. Mount socket portions of instruments 80 on holder stubs 29 in raised position of lid 4, with or without the lid structure being laterally released from the holding ring member 18. Press an operation start button when instruments are mounted and lid 4 is centered so as to be lowerable into its closed position according to FIG. 4.

2. Actuate water pump 50 for effecting water flushing through both pairs of rod and instrument channels 38, 82 and 42, 84, respectively. Hereby both of the channels 82 and 84 are cleaned by water flushing, but it has been found that this cleaning is enhanced when it is effected as a pulsating series of water and air flushing, and for this reason the valves V2 and V3 are operable to connect the channels with the source 46 of compressed air, such that the desirable pulsation between water and air is achievable e.g. 3–5 times.

3. By the latter operation some amount of water will have entered the treating chamber 22, and it is desirable, at this stage, to effect a rapid pumping or pressing out of the potentially contaminated water. For this purpose the bottom outlet valve V9 as connected with the bottom channel 76 is opened, and at the same time the pressurized air from the source 46 is let into the treating chamber 22 through the valve V1 and the channel 48, such that the collected water in the chamber 22 will be forced out through the drain channel 16.

4. The oil pump 60 is actuated so as to fill a small volume of oil into the channel between the valve V2 and the point 64, whereafter the valve V2 is opened so as to permit compressed air to blow the oil volume through the relevant channels and into the drive channel 82 of the instrument(s).

5. The valve V4 is opened, and the water pump 50 is actuated to sill a desired amount of water into the treating chamber 22 through the channel 58. Then the valve V1 is actuated intermittently so as to cause pulses of compressed air to blow up through the channel 48 and through a number of similar channels provided in the bottom plate 36 in an annular row, whereby the water is splashed up against the instruments. The top valve V8 is kept open for letting out the air. This pulsating cleaning operation is continued through a user-defined period of time.

6. Operation 2 is repeated.

7. Operation 3 is repeated.

8. With the top valve V8 open, and the valve V opened, the steam pump 66 is actuated to supply water to the steam generator chamber 68, in which the heater element 70 is switched on for conversion of the water into steam, which is injected into the chamber 22 through channel 72. The air inside the chamber 22 will be displaced out through the venting valve V8.

9. At some 107° C. all air will have left the chamber 22, and the valve V8 is closed. The steam generation is continued so as to build up temperature and pressure in the chamber 22.

10. When a preset temperature/pressure, e.g. 134° C./2.1 bar, has been reached, the two outlet valves V6 and V7 are opened and closed in an alternating manner, whereby for each opening the high pressure in the chamber 22 will force out steam through the respective instrument channels 82 and 84 from the outer ends thereof and through the respective rod channels 38 and 42 to the valves V6 and V7 and therefrom to the drain 44. This is the highly characteristic step previously referred to, causing air pockets in the instrumental channels to be driven out. During each opening sequence the pressure in the chamber 22 and therewith the temperature will drop somewhat, and before the next opening sequence it is ensured that the steam generator re-establishes the 134° C. in the chamber 2, Preferably, each of the channels 82 and 84 is subjected to such a blow-through of steam four times.

11. After the last operation of step 10 the chamber 22 is again steam heated to 134° C., and this temperature is maintained for as long as required, not less than 3 operation minutes for 134° C. program.

12. Operation 10 is repeated.

13. After the last through-flushing the outlet valve V9 is opened to allow steam and condensate to be drained from the chamber 22. When the temperature therein drops to e.g. 104° C. and the overpressure is less than 0.1 bar, the lid 4,28 and therewith the instruments 80 is lifted by actuation of the actuator means for raising the rods 20, and a new operation cycle can be initiated upon removal of the sterilized instruments 80.

What is claimed is:

1. An apparatus for disinfecting and sterilizing dental handpieces, comprising a treating chamber with internal holding stub means for receiving one or more dental handpieces, said holding stub means having through-channels for connecting exterior treatment fluid source means to internal standard channels in and through said handpieces in order to enable a through-flushing of treatment fluid through the internal standard channels from a socket end to a tip end of said handpieces;

said treating chamber being laid-out as a pressure resistant autoclaving chamber which through a channel comprising valve means is associated with external steam generating means for effectively filling the chamber with steam at elevated temperature and pressure such treating chamber also being associated with a venting valve to displace air inside the chamber during initializing of the treating chamber with steam, wherein said apparatus comprises outlet valve means which are designed to be opened and closed in an alternating manner, which valves are connected to said through-channels of said holding stub means whereby said alternative operating said outlet valve means for each opening causes the high pressure to force out steam through the respective instrument channels to the exterior atmosphere so as to enable back-flushing of pressurized steam from said treating chamber through said internal channels from the tip end to the socket end thereof, and said steam generating means is external of the treating chamber.

2. An apparatus as claimed in claim 1, in which said external steam generating means is an external steam generator connectable directly with the treating chamber and operable to at least periodically generate steam at a temperature/pressure level higher than required in the treating chamber in order to rapidly reestablish operational temperature/pressure upon each back-flushing operation.

3. An apparatus according to claim 1, in which said holding stubs are provided with at least two through-channels for selectively supplying treating fluid to at least two different internal channels of said instruments, said outlet valve means being operable to effect steam back-flushing through the individual through-channels in an alternating manner through one through channel at a time.

4. An apparatus according to claim 1, in which means are provided for supplying a cleaning liquid such as water to build up a bottom layer of the liquid in the treating chamber, and in which the bottom of the treating chamber has a number of upwardly directed air nozzles connected with an external source of compressed air through valve means operable to admit the compressed air to said nozzles in a pulsating manner to effect liquid splashing against the exterior of the instruments as held in positions above said liquid layer.

5. The apparatus according to claim 1 wherein the outlet valve means comprises two outlet valves.

* * * * *